United States Patent
Sarver et al.

(10) Patent No.: US 8,061,837 B2
(45) Date of Patent: Nov. 22, 2011

(54) PROGRESSIVE CHROMATIC ABERRATION CORRECTED OCULAR LENS

(76) Inventors: Edwin J. Sarver, Carbondale, IL (US); Donald R. Sanders, Elmhurst, IL (US)

(*) Notice: Subject to any disclaimer, the term of this patent is extended or adjusted under 35 U.S.C. 154(b) by 59 days.

(21) Appl. No.: 12/469,501

(22) Filed: May 20, 2009

(65) Prior Publication Data

US 2010/0103371 A1  Apr. 29, 2010

Related U.S. Application Data

(60) Provisional application No. 61/054,708, filed on May 20, 2008.

(51) Int. Cl.
*G02C 7/10* (2006.01)
*G02C 7/02* (2006.01)

(52) U.S. Cl. .................. 351/163; 351/165; 351/177

(58) Field of Classification Search ............ 351/163, 351/165, 213
See application file for complete search history.

(56) References Cited

U.S. PATENT DOCUMENTS

| | | | | |
|---|---|---|---|---|
| 6,305,801 B1 * | 10/2001 | Kerns et al. | ........... | 351/162 |
| 6,338,559 B1 * | 1/2002 | Williams et al. | ........... | 351/212 |
| 7,364,291 B2 * | 4/2008 | Haywood et al. | ........... | 351/163 |
| 7,641,337 B2 * | 1/2010 | Altmann | ........... | 351/165 |

* cited by examiner

*Primary Examiner* — Jordan Schwartz
(74) *Attorney, Agent, or Firm* — McHale & Slavin, P.A.

(57) ABSTRACT

A method to reduce ocular chromatic aberrations using a lens or other spatial structure to selectively band-pass filter transmitted light of certain wavelengths. The ocular lens overcomes the negative effects of the wavelength band pass filter lenses while maintaining its ability to reduce the negative effects of chromatic aberration. The band-pass filter is applied in one or more concentric zones and or angular regions. The lens power is adjusted in concert with the band-pass filter wavelength to minimize aberrations. Variations include the application of the band-pass filter being applied to an angular region and no filter is applied to another. Alternatively the band-pass filter is not applied to one or more concentric ring regions and is applied to one or more angular regions. The band-pass filter can be applied to the surface of the lens or spatial structure, or applied to the lens material.

12 Claims, 3 Drawing Sheets

PROGRESSIVE CHROMATIC ABERRATION CORRECTED OCULAR LENS

RELATED APPLICATIONS

This application claims the benefit under 35 U.S.C. 119(e) of U.S. Provisional Patent Application No. 61/054,708, filed May 20, 2008, entitled, "PROGRESSIVE CHROMATIC ABERRATION CORRECTED OCULAR LENS", the entirety of which is incorporated herein by reference.

FIELD OF THE INVENTION

The present invention generally relates to systems and methods for vision correction.

BACKGROUND OF THE INVENTION

The human eye often suffers from aberrations such as defocus and astigmatism that must be corrected to provide acceptable vision to maintain a high quality of life.

Correction of these defocus and astigmatism aberrations can be accomplished using a lens. The lens can be located at the spectacle plane, at the cornea (a contact lens or corneal implant), or within the eye as a phakic (crystalline lens intact) or aphakic (crystalline lens removed) intraocular lens.

The correction of these basic aberrations of defocus and astigmatism is generally limited to a single wavelength of light, typically in the middle of the visible spectrum. But the eye must function in a polychromatic environment that contains a wide range of wavelengths. For a refractive element such as a lens, the refracting power of the lens varies with wavelength. This is because the index of refraction of the lens material varies with wavelength. Generally, as wavelength increases, the index of refraction decreases. This variation in aberrations with wavelength is referred to as chromatic aberration.

Two methods that have been employed to combat the effects of chromatic aberration are wavelength band pass filters and diffractive lenses. Wavelength band pass filters use a dye to pass a given wavelength or narrow band of wavelengths and absorb the other wavelengths. An example is the "blue blocker" lens which passes wavelengths around green/yellow and absorbs blue and red wavelengths. Assuming defocus and astigmatism are corrected, the resulting retinal image is noticeably sharper since the chromatic aberration for the blue and red rays are reduced or eliminated. A negative of this approach is that the color information in the environment is significantly reduced.

A second method to combat chromatic aberration is the use of diffractive lenses. These lenses use step discontinuities to cause phase changes that reduce chromatic aberrations. A negative is that the step discontinuities also reduce the quality of the retinal image.

Our goal is to describe an ocular lens that overcomes the negative effects of the wavelength band pass filter lenses while maintaining its ability to reduce the negative effects of chromatic aberration. We term our lens the progressive chromatic aberration corrected ocular lens.

SUMMARY OF THE INVENTION

A method to reduce ocular chromatic aberrations using a lens or other spatial structure to selectively band-pass filter transmitted light of certain wavelengths and overcome the negative effects of the wavelength band pass filter lenses while maintaining its ability to reduce the negative effects of chromatic aberration. The band-pass filter is applied in one or more concentric zones and or angular regions. The lens power is adjusted in concert with the band-pass filter wavelength to minimize aberrations. Variations include the application of the band-pass filter being applied to an angular region and no filter is applied to another. Alternatively the band-pass filter is not applied to one or more concentric ring regions and is applied to one or more angular regions. The band-pass filter can be applied to the surface of the lens or spatial structure, or applied to the lens material.

Thus, an objective of the invention is to provide a progressive chromatic aberration corrected ocular lens.

Another objective of the invention is teach the use of an ocular lens that overcomes the negative effects of the wavelength band pass filter lenses while maintaining its ability to reduce the negative effects of chromatic aberration.

Still another objective of the invention is to disclose a method to reduce ocular chromatic aberrations using a lens or other spatial structure to selectively band-pass filter transmitted light of certain wavelengths.

Still another objective of the invention is to disclose a method to reduce ocular chromatic aberrations where the band-pass filter is applied in one or more concentric zones.

Yet still another objective of the invention is to disclose a method to reduce ocular chromatic aberrations where the band-pass filter is applied in angular regions.

Another objective of the invention is to disclose a method to reduce ocular chromatic aberrations where the local lens power is adjusted in concert with the band-pass filter wavelength to minimize aberrations.

Still another objective of the invention is to disclose a method to reduce ocular chromatic aberrations where the band-pass filter is applied to an angular region and no filter is applied to another.

Yet still another objective of the invention is to disclose a method to reduce ocular chromatic aberrations where the band-pass filter is not applied to one or more concentric ring regions and is applied to one or more angular regions.

A further objective of the invention is to disclose a method to reduce ocular chromatic aberrations where the band-pass filter is applied to the surface of the lens or spatial structure.

Still another objective of the invention is to disclose a method to reduce ocular chromatic aberrations where the band-pass filter is applied to the lens material.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

Figure 1:
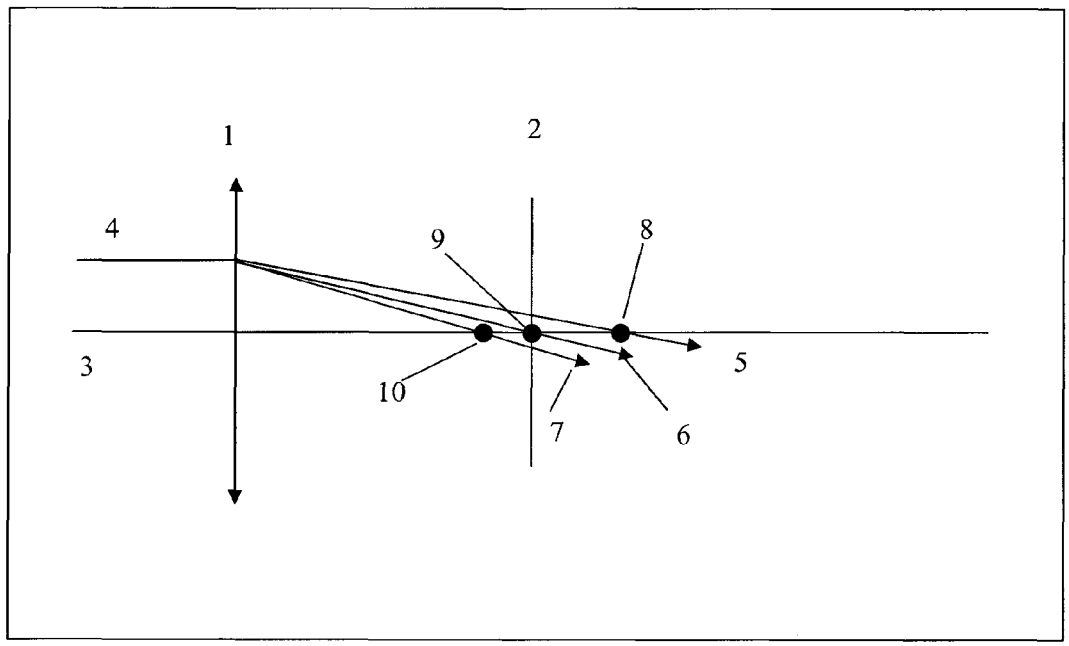
FIG. 1 is a paraxial model for a chromatic eye.

wherein the center of the lens is unfiltered and the center region the top half of the lens is band-pass filtered.

DETAILED DESCRIPTION OF THE PREFERRED EMBODIMENT

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

A simple paraxial model for a chromatic eye is illustrated in FIG. 1. In FIG. 1, a single lens 1 which represents all refractive elements of the corrected eye and an image plane 2 which represents the retina are positioned along an optical axis 3. An incoming chromatic ray 4 contains red, green, and blue wavelengths and is refracted by lens 1. After refraction, three rays emerge from lens 1 corresponding to the three wavelengths. Ray 5 represents the path taken by the red wavelength, ray 6 represents the path taken by the green wavelength, and ray 7 represents the path taken by the blue wavelength. Since this is a simple polychromatic paraxial model, there are three distinct focus points. Point 8 represents the focus point for the red wavelength, point 9 represents the focus point for the green wavelength, and point 10 represents the focus point for the blue wavelength. The transverse chromatic aberration present for this input ray 4 is given by the distance from the optical axis 3 to the locations where the red ray 5 and blue ray 7 cross the image plane 2. The transverse chromatic aberration is dependent upon the height of the incoming ray 4.

Figure 2:
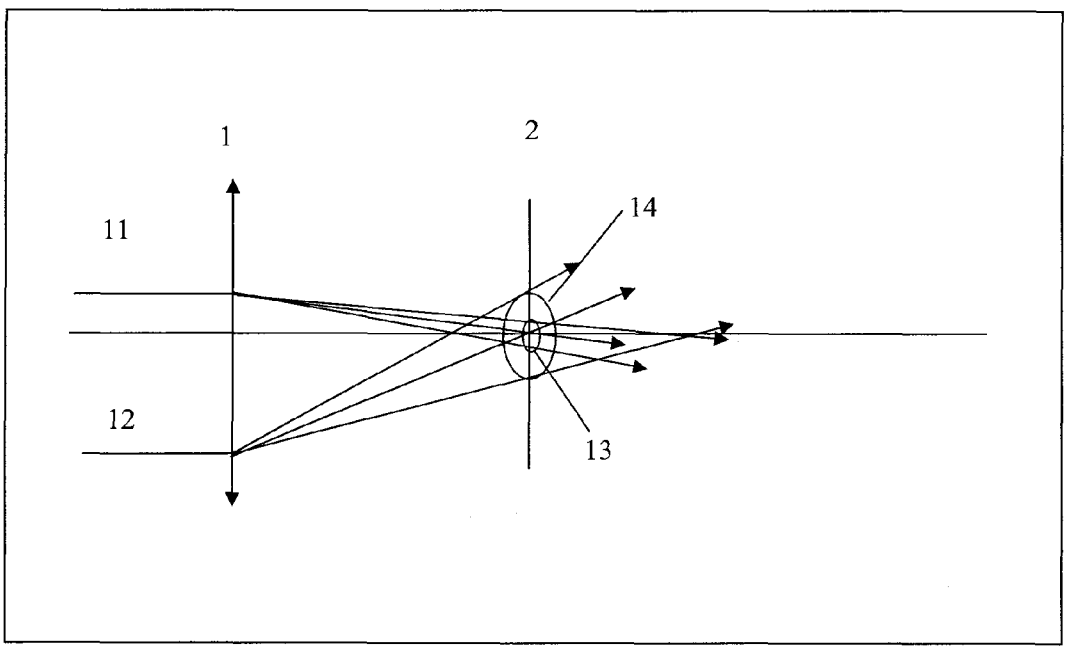
FIG. 2 is an illustration of transverse chromatic aberration with an incoming ray with small height and a ray with large height.

In FIG. 2 an incoming ray 11 with small height and a ray 12 with large height are illustrated. As can be seen in the figure, the amount of transverse chromatic aberration is smaller for incoming ray 11 (see ellipse 13) compared to incoming ray 12 (see ellipse 14). This observation is the basis for progressive chromatic aberration correct ocular lens (PCACL).

Incident rays near the optical axis will produce small amounts of transverse chromatic aberration. These rays are permitted to pass through the eye unfiltered so as to provide a full visible spectrum to the retina (color image). Incident rays far from the optical axis produce large amounts of transverse chromatic aberration. These rays are filtered to pass a narrow band of wavelengths around the green-yellow wavelength. Thus, these more displaced rays still provide visual information while eliminating chromatic aberration at the expense of eliminating color information. This situation is illustrated in FIG. 3.

Figure 3:
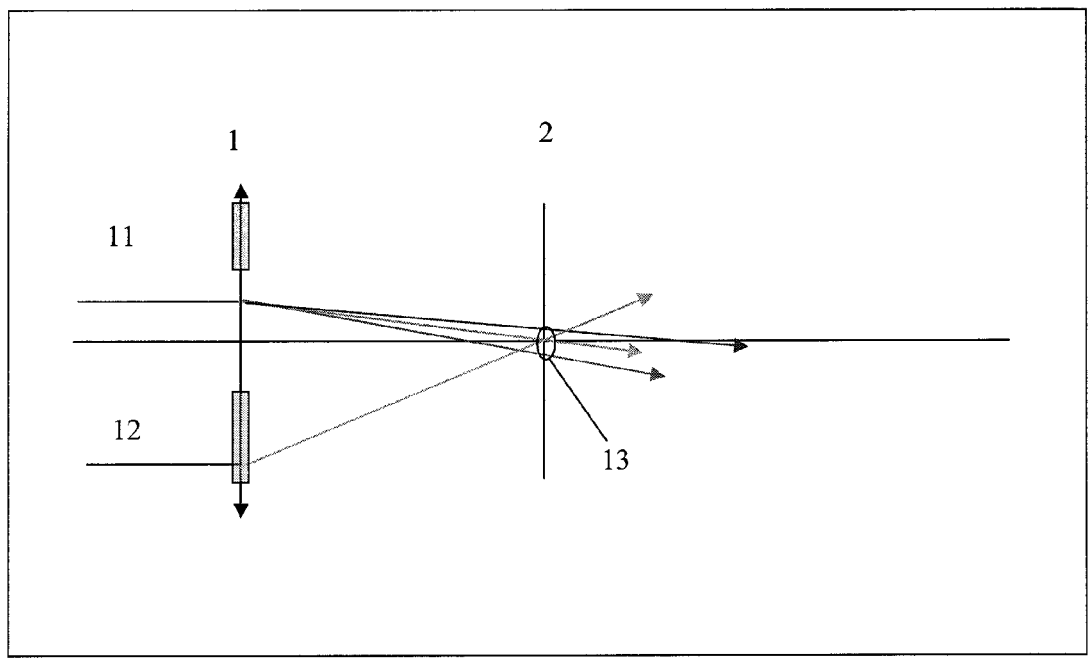
FIG. 3 is an illustration of a wavelength band-pass filter applied to rays.

As indicated in FIG. 3, the addition of the wavelength band-pass filter applied to the rays further from the optical axis provides a tighter focus (ellipse 13) than that provided when the filter is not present (ellipse 14 in FIG. 2). At the same time a better focus is provided, a full color image is provided (for central rays) to the retina.

Figure 4:
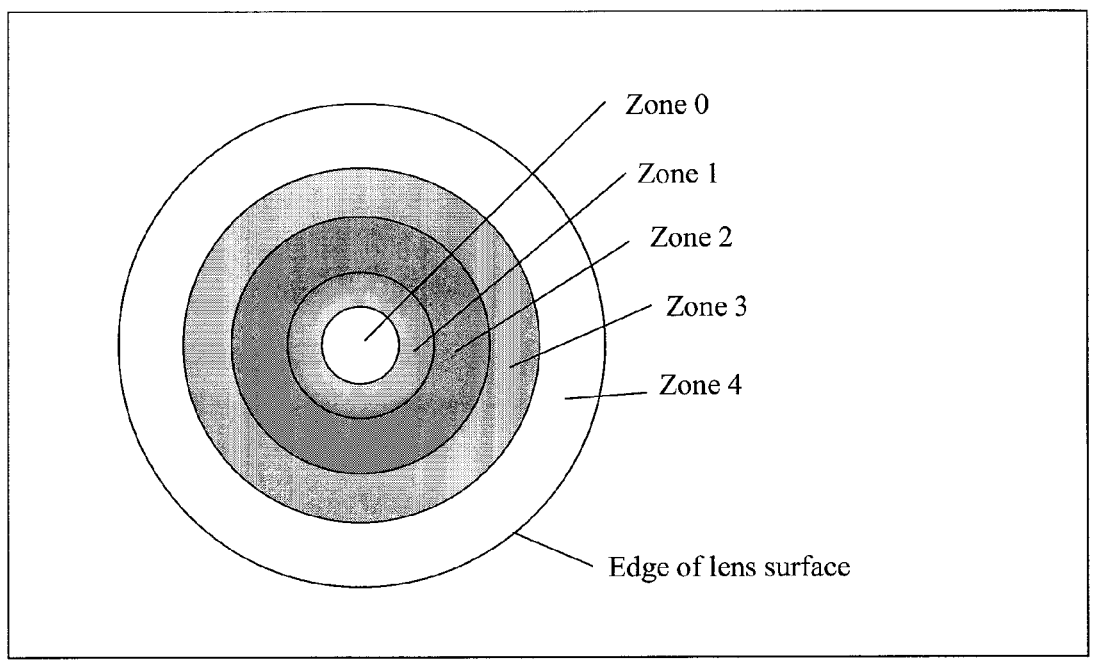
FIG. 4 is an illustration of a wavelength selective band-pass filter.

The application of the wavelength selective band-pass filter is detailed in FIG. 4. In this figure the five zones cover the surface of the lens from the center to the edge of the lens. Zone 0 is the central unfiltered region that allows all rays to pass without being attenuated. Zone 2 is the primary band-pass region that only allows rays in the green-yellow wavelengths to reach the retina. Zones 1 and 3 are transition zones. Zone 1 provides a smooth transition from the no-filtered region in Zone 0 to the band-pass filtered region of Zone 2. Likewise, Zone 3 provides a smooth transition from the band pass filtered region of Zone 2 to the unfiltered region in Zone 4. The primary purpose of Zone 4 being unfiltered (like Zone 0) is because rays very far from the optical axis tend to be outside the eye's entrance pupil and hence filtered the rays will have no affect since these rays will not reach the retina.

The central unfiltered region is selected so that the amount of chromatic blur (ellipse 13 in FIGS. 2 and 3) is not objectionable to the subject. This criterion could include simple blur considerations, the Stiles-Crawford effect, and other individual optical or psychological preferences. In the preferred embodiment, this zone diameter is 2.0 mm.

In the preferred embodiment, zones 1, 3, and 4 are not used, while zone 2, the primary band-pass region, begins just outside the central zone and continues to the periphery of the lens.

Other combinations of the profile zones are possible and would be warranted depending upon the lens location (spectacle, contact lens, or implanted lens), patient's pupil size, and individual optical and psychological preferences of the patient.

In the above description a single wavelength band-pass filter zones is described. In the preferred embodiment, the peak of the band-pass filter will be centered on the wavelength to which the human eye is most sensitive. In the preferred embodiment, the width of the band-pass filter is such that the transverse chromatic aberration of incident rays distant from the optical axis are not objectionable.

Figure 5:
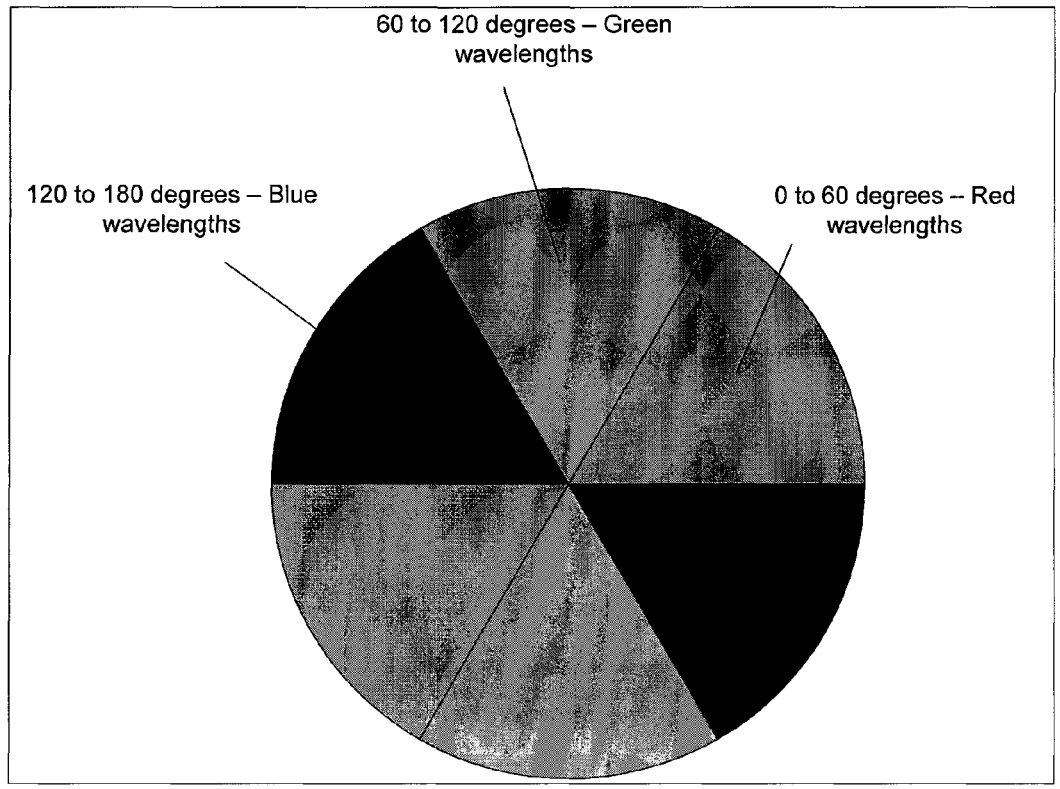
FIG. 5 is illustration of the band-pass filter over angular regions.

Band-pass filters with the peak wavelength other than that which the human eye is most sensitive to could also be used. The selection of band-pass filter for a given zone could, for example, be made in concert with the optical design of the lens. That is, suppose the center of the lens is designed to focus red wavelengths, the mid-periphery to focus green wavelengths, and the periphery to focus blue wavelengths. The matching band-pass filter would then allow only red, green, or blue rays through in those regions. Instead of concentric circle regions, the same principle could apply for radial sections. That is the lens could be designed to focus red rays in meridians from 0 to 60 degrees, to focus green rays in meridians 60 to 120 degrees, and blue rays in meridians 120 to 180 degrees. The matching band-pass filters would then be placed over these angular regions. This second method has the benefit of passing a color image to the retina without chromatic aberration and the benefit is independent of pupil size. This application of the band-pass filter over angular regions is illustrated in FIG. 5.

A particular case of applying a band-pass filter over a given angular extent is where the band-pass filter is applied over one half of the lens surface and no filter is applied over the other. This will have the effect of cutting the chromatic aberrations in half while allowing color information from half of the incident light. In a binocular ocular system, such as both eyes, the filter could be placed in, for example, the top half in the lens in one eye and the bottom half in the lens in the other eye. This would rely on the brain to select the color information and reject the chromatic aberrations from the stereo images it processes.

Figure 6:
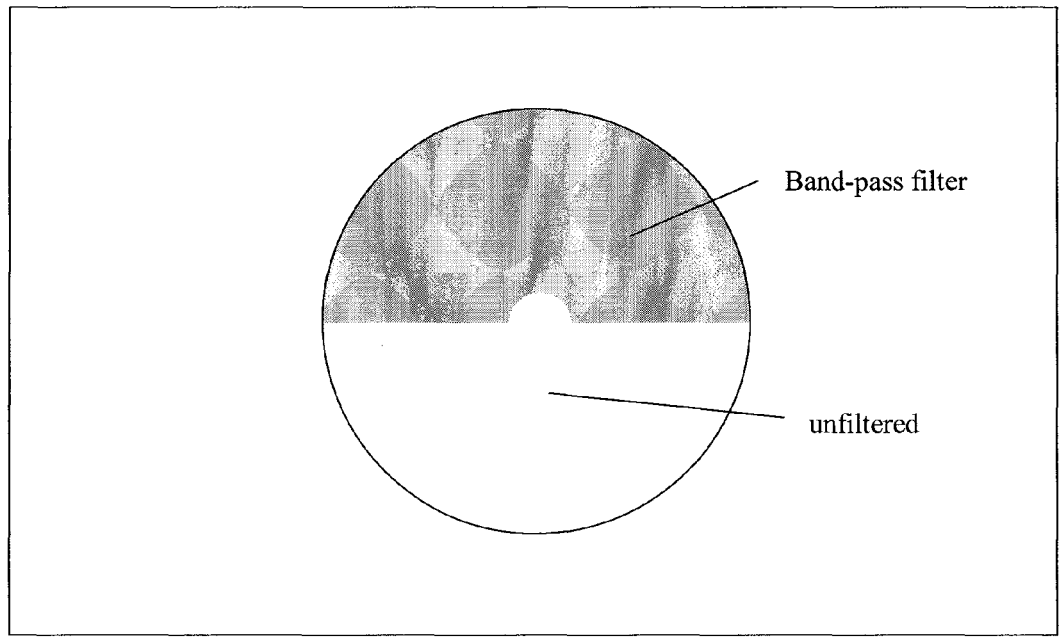
FIG. 6 is an illustration of a combination of concentric zones and angular regions for applying the band-pass filter(s)

A combination of concentric zones and angular regions for applying the band-pass filter(s) could be used. For example, the center of the lens could be unfiltered since these rays introduce very little chromatic aberrations, and outside this center region the top half of the lens could be band-pass filtered. This strategy is illustrated in FIG. 6.

Alternatively, the band pass filters could be applied to the surface and/or to the material of the lens.

Further, the reduction of chromatic aberrations does not have to be applied to a lens. It could be applied to some other spatial structure such as a flat window placed at the spectacle plane, corneal plane, or implanted within the eye.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification.

One skilled in the art will readily appreciate that the present invention is well adapted to carry out the objects and obtain the ends and advantages mentioned, as well as those inherent therein. Any compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

We claim:

1. A method of reducing ocular chromatic aberrations comprising:
   positioning an optical wavelength filter between an object being viewed and a pupil of an eye;
   selectively filtering the wavelengths of light transmitted from an object to a pupil of an eye depending on the distance which a ray of light is from an optical axis, and transmitting only certain wavelengths of light to said pupil, wherein said optical wavelength filter is used in conjunction with a lens and wherein a power of said lens is adjusted in concert with said optical wavelength filter thereby minimizing aberrations, whereby chromatic aberrations are substantially reduced.

2. The method of claim 1 including employing a plurality of concentric zones in said optical wavelength filter.

3. The method of claim 2 including filtering said optical wavelengths in at least one of said concentric zones and not filtering said optical wavelengths in at least one other of said concentric zones.

4. The method of claim 3 including filtering said optical wavelengths in one of said concentric zones and not filtering said optical wavelengths in said remaining concentric zones.

5. The method of claim 3 including not filtering said optical wavelengths in one of said concentric zones and filtering said optical wavelengths in said remaining concentric zones.

6. The method of claim 1 including filtering said optical wavelengths is performed on said lens.

7. An ocular device for reducing ocular chromatic aberrations comprising:
   an optical wavelength filter positioned between an object being viewed and a pupil of an eye;
   a filter which selectively filters the wavelengths of light transmitted from an object to a pupil of an eye depending on the distance which a ray of light is from an optical axis,
   wherein said optical wavelength filter is used in conjunction with an ocular lens and wherein a power of said ocular lens is adjusted in concert with said optical wavelength filter thereby minimizing aberrations,
   whereby only certain wavelengths of light are transmitted to said pupil and chromatic aberrations are substantially reduced.

8. The ocular device of claim 7 including a plurality of concentric zones in said optical wavelength filter.

9. The ocular device of claim 8 wherein at least one of said concentric zones includes said optical wavelength filter and at least one other of said concentric zones does not include said optical wavelength filter.

10. The ocular device claim 9 wherein one of said concentric zones includes said optical filter and said remaining concentric zones do not include said optical filter.

11. The ocular device of claim 9 wherein one of said concentric zones does not include said optical filter and said remaining concentric zones include said optical filter.

12. The ocular device of claim 7 including said optical filter on a surface of said ocular lens.

* * * * *